(12) United States Patent
Kim et al.

(10) Patent No.: US 8,277,635 B2
(45) Date of Patent: Oct. 2, 2012

(54) ELECTROCHEMICAL BIOSENSOR MEASURING SYSTEM

(75) Inventors: Moon Hwan Kim, Seoul (KR); Keun Ki Kim, Seoul (KR); Gang Cui, Seoul (KR); Hakhyun Nam, Seoul (KR); Geun Sig Cha, Seoul (KR)

(73) Assignee: I-Sens, Inc., Seoul (KR)

( * ) Notice: Subject to any disclaimer, the term of this patent is extended or adjusted under 35 U.S.C. 154(b) by 449 days.

(21) Appl. No.: 12/530,128

(22) PCT Filed: Feb. 26, 2008

(86) PCT No.: PCT/KR2008/001104
§ 371 (c)(1),
(2), (4) Date: Sep. 4, 2009

(87) PCT Pub. No.: WO2008/111742
PCT Pub. Date: Sep. 18, 2008

(65) Prior Publication Data
US 2010/0126882 A1    May 27, 2010

(30) Foreign Application Priority Data
Mar. 14, 2007    (KR) .................. 10-2007-0025106

(51) Int. Cl.
*G01N 27/327* (2006.01)
*G01N 27/403* (2006.01)
*G01N 27/26* (2006.01)
*G01N 33/53* (2006.01)

(52) U.S. Cl. ................ 205/775; 205/777.5; 204/403.02; 204/403.14

(58) Field of Classification Search ..... 204/400–403.15; 205/775, 777.5, 787, 792
See application file for complete search history.

(56) References Cited

U.S. PATENT DOCUMENTS
5,118,369 A * 6/1992 Shamir .......................... 156/64
(Continued)

FOREIGN PATENT DOCUMENTS
EP    1288653 A1    3/2003
(Continued)

OTHER PUBLICATIONS
International Search Report of the International Searching Authority, mailed Jun. 10, 2008, for corresponding International Application No. PCT/KR2008/001104.

(Continued)

*Primary Examiner* — Jeffrey T Barton
*Assistant Examiner* — Jennifer Dieterle
(74) *Attorney, Agent, or Firm* — Klarquist Sparkman, LLP

(57) ABSTRACT

Disclosed herein is an electrochemical biosensor measuring device which comprises at least two photodiodes for emitting light beams at regular time intervals in a sequential manner, with the insertion of an electrochemical biosensor thereto, and a detector for sensing the emitted light beams, thereby identifying the production lot information recorded on a production lot information identification portion on the electrochemical biosensor. Thus, the device enjoys economic advantages of not requiring a high-priced optical filter in detecting the light absorbed through or reflected from the production identification information recorded in biosensor and a complicated software algorithm to recover the production lot information. Also, the measuring device automatically identifies the production lot information recorded on the biosensor, so that the frequency of inconvenience and error that occur when a user personally inputs the production lot information of the biosensor can be reduced, with the result that the measured values can be conveniently and accurately acquired.

7 Claims, 2 Drawing Sheets

U.S. PATENT DOCUMENTS

| | | | |
|---|---|---|---|
| 5,362,953 A * | 11/1994 | McKenna et al. | 235/462.49 |
| 6,203,069 B1 * | 3/2001 | Outwater et al. | 283/88 |
| 6,543,693 B1 | 4/2003 | Stern et al. | |
| 6,616,819 B1 * | 9/2003 | Liamos et al. | 204/403.02 |
| 6,770,487 B2 * | 8/2004 | Crosby | 436/518 |
| 6,814,844 B2 * | 11/2004 | Bhullar et al. | 204/403.01 |
| 6,867,051 B1 | 3/2005 | Anderson et al. | |
| 7,185,816 B1 * | 3/2007 | Shoobridge | 235/462.04 |
| 2002/0060247 A1 | 5/2002 | Krishnaswamy et al. | |

FOREIGN PATENT DOCUMENTS

| | | |
|---|---|---|
| EP | 1764153 A2 | 3/2007 |
| EP | 1974817 A2 | 10/2008 |
| JP | 63-065588 | 3/1988 |
| JP | 07-057039 | 3/1995 |
| JP | 2003-149192 | 5/2003 |
| JP | 2004-030383 | 1/2004 |
| JP | 2006-215034 | 8/2006 |
| KR | 1020010101855 A | 11/2001 |
| KR | 1020060124112 A | 12/2006 |
| KR | 10-0680267 | 2/2007 |
| KR | 10-2008-0080841 | 9/2008 |
| WO | WO2008/108548 A1 | 9/2008 |

OTHER PUBLICATIONS

Bauman et al., "Preparation of Immobilized Cholinesterase for Use in Analytical Chemistry," *Analytical Chemistry*, vol. 37, No. 11, pp. 1378-1381, Oct. 1965.

Cassidy et al., "Novel Electrochemical Device for the Detection of Cholesterol or Glucose," *Analyst*, vol. 118, pp. 415-418, Apr. 1993.

K. B. Oldham, "Steady-State Voltammetry" in *Microelectrodes: Theory and Applications*, Trent University, Peterborough, Canada, Kluwer Academic Publishers, pp. 35-50, 1991.

European Patent Office, "Supplementary European Search Report" for European Application No. EP08723142, Jun. 27, 2011, 2 pages.

* cited by examiner

ELECTROCHEMICAL BIOSENSOR MEASURING SYSTEM

CROSS REFERENCE TO RELATED APPLICATIONS

This is the U.S. National Stage of International Application No. PCT/KR2008/001104, filed Feb. 26, 2008, which in turn claims the benefit of and priority to Korean Patent Application No. KR10-2007-0025106, filed Mar. 14, 2007.

TECHNICAL FIELD

The present invention relates to an electrochemical biosensor measuring device.

BACKGROUND ART

For the diagnosis and prophylaxis of diabetes mellitus, the importance of periodically monitoring blood glucose levels is increasingly emphasized. Nowadays, strip-type biosensors designed to be used in hand-held reading devices allow individuals to readily monitor glucose levels in blood.

A large number of commercialized biosensors measure the blood glucose content of blood samples using an electrochemical technique. The principle of the electrochemical technique is based on the following Reaction 1.

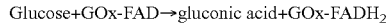

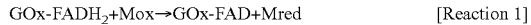 [Reaction 1]

wherein, GOx represents glucose oxidase; GOx-FAD and GOx-FADH$_2$ respectively represent an oxidized and a reduced state of glucose-associated FAD (flavin adenine dinucleotide), a cofactor required for the catalysis of glucose oxidase; and Mox and Mred denote the oxidized and reduced states of an electron transfer mediator, respectively.

The electrochemical biosensor uses as electron transfer mediators organic electron transfer materials, such as ferrocenes or their derivatives, quinines or their derivatives, organic or inorganic materials containing transition metals (hexaamine ruthenium, polymers containing osmium, potassium ferricyanide and the like), organic conducting salts, and viologens.

The principle of measuring blood glucose using the biosensor is as follows.

Glucose in the blood is oxidized to gluconic acid by the catalysis of the glucose oxidase, with the cofactor FAD reduced to FADH$_2$. Then, the reduced cofactor FADH$_2$ transfers electrons to the mediator, so that FADH$_2$ returns to its oxidized state; that is, FAD and the mediator are reduced. The reduced mediator is diffused to the surface of the electrodes. The series of reaction cycles is driven by the anodic potential applied at the working electrode, and redox current proportional to the level of glucose is measured. Compared to biosensors based on colorimetry, electrochemical biosensors (that is, based on electrochemistry) have the advantages of not being influenced by the turbidity or color of the samples and allowing the use of wider range of samples, even cloudy ones, without pretreatment thereof.

Although this electrochemical biosensor is generally convenient when used to monitor and control the amount of blood glucose, its accuracy is greatly dependent on the lot-to-lot variation between respective mass-production in which the biosensors are produced. In order to eliminate such variation, most of the commercialized biosensors are designed such that a user directly inputs calibration curve information, which is predetermined at the factory, into a measuring device capable of reading the biosensor. However, this method inconveniences the user a great deal and causes the user to make input errors, thus leading to inaccurate results.

In order to solve this problem, a method by which the resistance of each electrode can be adjusted such that the variations in mass production is corrected (US20060144704A1), a method in which a conductor is printed in a bar code fashion on the biosensor strip to record the production information (U.S. Pat. No. 6,814,844), a method in which a connection to a resistor bank is made (WO2007011569A2), and a method by which information is read by varying resistance through the adjustment of the length or thickness of each electrode (US20050279647A1) have been proposed. The methods proposed for the electrochemical biosensors are all based on a technique in which electrical variation is read. Furthermore, a method for distinguishing production lot information by reading the resistivity of a conductor marked on a strip using an electrical method (U.S. Pat. No. 4,714,874) has been proposed.

However, these methods function to accurately adjust resistance, and require a process of mass-producing the sensors first, measuring the statistical characteristics of the sensors, and post-processing the measured information again using a method of adjusting the resistance marked on the sensors. However, the process of accurately adjusting the resistance, marked in large quantities, through the post-processing is very inconvenient, and is difficult to use in practical applications.

Methods in which colored marks are used with a spectral system capable of discriminating colors to realize a colorimetric method (U.S. Pat. No. 3,907,503, U.S. Pat. No. 5,597,532, U.S. Pat. No. 6,168,957), a method in which a plurality of color marks is read at various wavelengths of visible and infrared ray regions using a spectroscope (U.S. Pat. No. 5,945,341), and a method capable of reading bar codes (EP00075223B1, WO02088739A1) have been proposed. These methods using color or bar codes are favorable for a colorimetric method-based sensor using the spectrum system, but they have technical and economic difficulties when applied to a system using an electrochemical measurement mechanism. For example, the size and structure of a portion where the electrochemical sensor strip is inserted into the measuring device for the purpose of electrical connection, that is, a connection space of the sensor strip, is very limited in constructing a device and circuit for spectroscopically identifying a structure into which the production lot information is input. Further, as shown in FIG. 1, because a light emitter-detector system is operated in a manner such that the detector senses the light reflected by or transmitted through a production lot information identification portion to which light is projected from photodiodes of various colors, a process of scattering various wavelengths of the detected light using a filter is required to identify the information of the light, which makes the calculation process, the device, and the program complicated. Thus, the expense for constructing the system is greatly increased.

Furthermore, instead of the methods of marking the production lot information on the sensor strip, a method of recording information on a container or pack containing a sensor and allowing the information to be read by the measuring device (EP0880407B1) has been proposed. However, this method also has a possibility of causing the user to make an error in which a code recorded on the container is incorrectly read.

Leading to the present invention, intensive and thorough research into electrochemical biosensors, conducted by the present inventors, aiming to maintain economic efficiency in the construction of the measuring device while allowing the mass production of an electrochemical biosensor in which the production lot information thereof can be easily and accurately input into the measuring device and which removes the risk of mistakes being made by the user, thus providing an accurate measurement value, resulted in the finding that, when the production lot information is recorded on the electrochemical biosensor strip using infrared absorption/reflection marks and when a production lot information identification portion, at which the production lot information is recorded on the electrochemical biosensor strip, is identified in the measuring device, there is no need to use a high-priced filter in the case where photodiodes of various colors sequentially emit light at regular time intervals, so that the light emitter-detector system has a simple construction and is formed on the same printed circuit board (PCB) of measuring device, and thus can not only reduce a complicated calculation process performed for post-treatment but also maintain economic efficiency in the construction of the measuring device.

DISCLOSURE OF INVENTION

Technical Problem

Accordingly, the present invention has been made keeping in mind the above problems occurring in the prior art, and an object of the present invention is to provide an electrochemical biosensor measuring device comprising at least two light emitters emitting light at regular time intervals and a detector for sensing the light from the light emitters, which, when the electrochemical biosensor is inserted into the measuring device without a mistake being made by a user, automatically identifies the production lot information of the biosensor, thus enabling blood glucose to be conveniently and accurately measured and being economical.

Technical Solution

In order to accomplish the above object, the present invention provides an electrochemical biosensor measuring device, which measures an electrochemical biosensor composed of plurality of electrodes including at least a working electrode and an auxiliary electrode prepared on at least one or two insulating plates; a capillary sample cell for introducing a sample into the electrodes; a reaction reagent layer, formed on the working electrode, containing a redox enzyme and an electron transfer mediator; an electrical connection portion for connecting the working electrode and the auxiliary electrode; and a production lot information identification portion configured such that production lot information is recorded on at least one insulating plate, which is selected from among at least two planar insulating plates and does not interrupt a connection between the electrodes, wherein the electrochemical biosensor measuring device comprises at least two light emitters sequentially emitting light at regular time intervals and a detector for sensing the emitted light, so as to identify the production lot information recorded on the production lot information identification portion.

In the specification, the term "biosensor" is used to have the same meaning as the term "biosensor strip".

Advantageous Effects

The electrochemical biosensor measuring device according to the present invention enjoys economic advantages of not requiring a high-priced optical filter in detecting the light absorbed through or reflected from the production identification information recorded in biosensor and a complicated software algorithm to recover the production lot information. Also, the measuring device automatically identifies the production lot information recorded on the biosensor, so that the frequency of inconvenience and error that occur when a user personally inputs the production lot information of the biosensor can be reduced, with the result that the measured values can be conveniently and accurately acquired.

BRIEF DESCRIPTION OF THE DRAWINGS

The above and other objects, features and advantages of the present invention will be more clearly understood from the following detailed description taken in conjunction with the accompanying drawings, in which.

BRIEF DESCRIPTION OF THE MARK OF DRAWINGS

Figure 1:
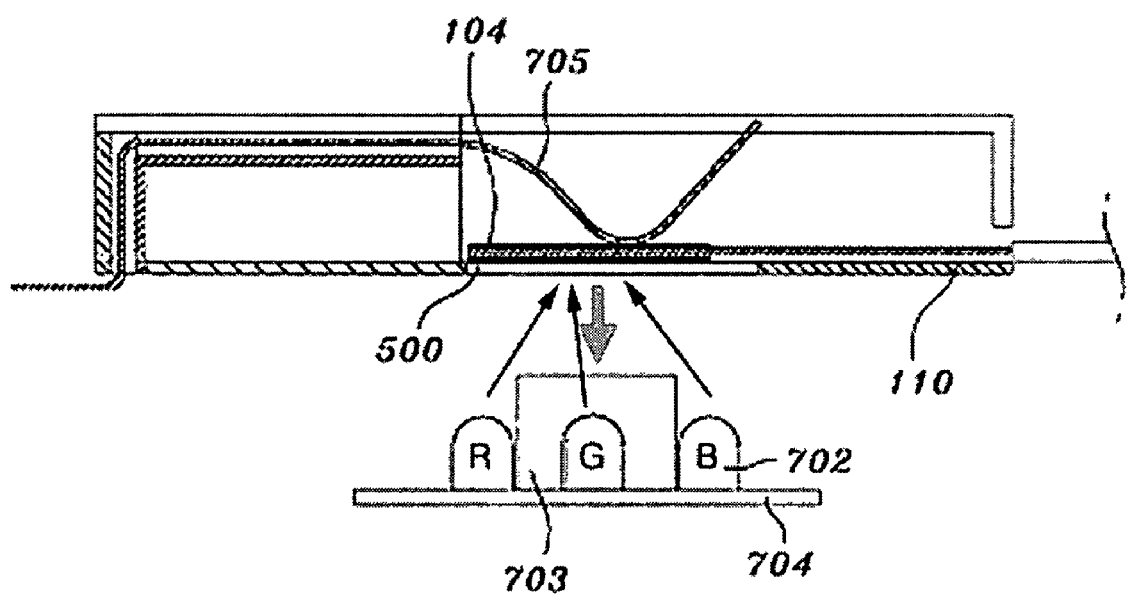
FIG. 1 is a schematic view showing a process of identifying production lot information on a biosensor on a conventional electrochemical biosensor measuring device.

104: electrode
110: biosensor strip
500: production lot information identification portion
702: light emitter
703: detector
704: printed circuit board
705: electrical connection portion

BEST MODE FOR CARRYING OUT THE INVENTION

The electrodes of the electrochemical biosensor used in the electrochemical biosensor measuring device according to the present invention may be formed on one or both of at least two planar insulating plates. That is, (1) a single working electrode and a single auxiliary electrode (or reference electrode) may be formed on the same planar insulating plate, or (2) may be formed on two planar insulating plates facing each other [parallel electrodes; reference: E. K. Bauman et al., Analytical Chemistry, vol 37, p 1378, 1965; K. B. Oldham in "Microelectrodes: Theory and Applications," Kluwer Academic Publishers, 1991; J. F. Cassidy et al., Analyst, vol 118, p 415].

In addition, the electrodes of the electrochemical biosensor used in the electrochemical biosensor measuring device according to the present invention may further include a sample fluidity determining electrode that is disposed behind the working electrode and is capable of measuring the fluidity of whole blood samples on a lower planar insulating plate.

The biosensor is described in greater detail taking parallel electrodes as an example.

In the case where the electrochemical biosensor used for the electrochemical biosensor measuring device according to the present invention is constructed using the parallel electrodes, the biosensor may have a structure in which the working electrode and the auxiliary electrode are spaced apart from each other by a pressure-adhesive spacer 50-250 μm thick, and are aligned or not aligned with each other while facing each other.

In the thin spacer, a capillary sample cell on a microliter volume scale is provided for injecting a bio-sample in a measurement space defined by the working electrode and the auxiliary electrode and retaining the sample therein. The capillary sample cell includes a sample introducing portion and a micro-path.

In the thin spacer, a sample fluidity determining electrode is placed preferably at a predetermined distance from the working electrode or the auxiliary electrode so that fluorinated blood having a corpuscle volume of 40% can reach the working electrode (or the auxiliary electrode) along a micro-path 0.5-2 mm wide and 50-250 μm high within about 600 ms, and more preferably at a predetermined distance from the working electrode or the auxiliary electrode such that non-fluorinated blood can reach the electrode along the micro-path 0.5-2 mm wide and 50-250 μm high within 300 ms, and far more preferably within 200 ms.

Functioning to introduce a blood sample into one end of the biosensor, the sample-introducing portion is preferably formed in a "L" shape so as to allow the rapid, accurate and convenient introduction of a blood sample from the fore end of the biosensor strip. The sample introducing portion is structured such that an allowance space is formed at a location at which a sample introducing path and an air vent are crossed. By the term "crossed", as used herein, it is meant that the sample-introducing path and the air vent are not arranged parallel to each other, but intersect each other at a predetermined point.

During measurement, the allowance space helps maintain a constant and accurate volume of the blood sample within the path while discharging the excess sample through the air vent. Also, the allowance space may be used as the place where the sample fluidity determining electrode is disposed. When introduced into the sample introducing portion, a blood sample moves to the electrodes through the micro-path.

In the electrochemical biosensor used in the electrochemical biosensor measuring device according to the present invention, the reaction reagent layer may formed merely by applying a reagent solution only to the working electrode, or to both the working electrode and the sample fluidity determining electrode. The reaction reagent layer includes an enzyme, such as a glucose oxidase or a lactate oxidase, an electron transfer mediator, a water-soluble polymer, such as a cellulose acetate, a polyvinyl alcohol or a polypyrrol, a fatty acid having 4 to 20 carbon atoms as a reagent for reducing a hematocrit effect, and a hydrophilic quaternary ammonium salt.

In the electrochemical biosensor according to the present invention, electrode connection portions at which the biosensor and the measuring device are electrically connected are designed to exist in the same plane in which the working electrode and auxiliary electrode are connected via connection lines. The level of blood glucose that is measured by the biosensor of the present invention from the results of an electrochemical reaction is provided to the measuring device through the electrode connection portions, and thus can be numerically converted into a precise blood glucose value.

The electrochemical biosensor according to the present invention includes a production lot information identification portion for providing calibration curve information about various concentrations of liquid samples, which is used for respective production lots at the time of manufacturing the biosensor, along with biosensor production lot information, to a user.

The production lot information identification portion may include one or more hue marks displaying the information about differences between production lots attributable to differences in color, brightness, or chroma. It is preferred that the number of hue marks be adjusted to fall within the range of 1 to 10.

In the electrochemical biosensor measuring device according to the present invention, the operational principle of identifying the production lot information identification portion in the measuring device is described in detail below.

In the measuring device, at least two light emitters, for examples, photodiodes, are integrated within a small space. Photodiodes useful in the present invention are preferably three-component light emitting diodes emitting red, blue and green colors, or four-component light emitting diodes emitting white, red, blue and blue colors, but are not limited thereto. The light emitted from the photodiodes is sensed by the production lot information identification portion of the biosensor. In this regard, the photodiodes with different wavelengths are preferably operated at regular time intervals in a sequential manner.

The light sensed by the production lot information identification portion is transmitted therethrough or reflected therefrom, experiencing a change in intensity or wavelength. The transmitted or reflected light is detected by a detector, such as an optical identifier, set at an intermediate location of the light emitters. The change in the intensity and wavelength of light, as detected by the detector, is delivered to a calculation system in which the change is converted into digital information. The converted digital information is combined to appear as the production lot information of the biosensor.

The two or more photodiodes emit light beams with different wavelengths in a sequential manner at regular time intervals. The light beams, originated from the emitters, containing the production lot information, can be detected in a sequential manner by a detector without a filter.

Figure 2:
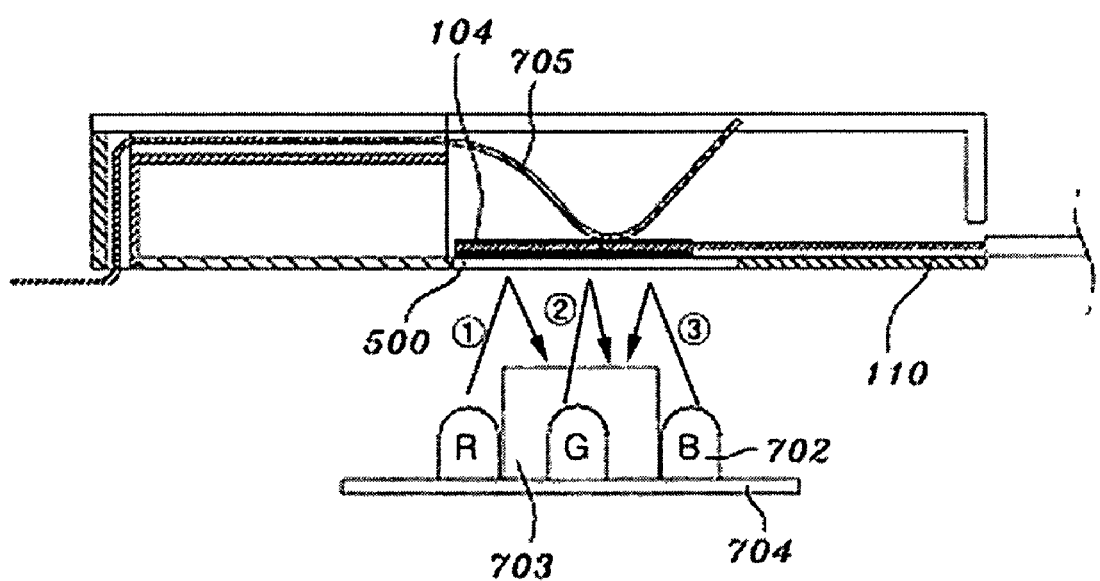
FIG. 2 is a schematic view showing a process of identifying production lot information on a biosensor on an electrochemical biosensor measuring device according to an embodiment of the present invention.

With reference to FIG. 2, a light emitter 700 is composed of three-component photodiodes emitting red (R), green (G) and blue (B) colors. When it is radiated on a production lot information identification portion 500, the red light is transmitted through or reflected from the production lot information identification portion 500 and sensed by a detector 703, in which the change in the intensity and wavelength of the light is converted into digital information. Next, the green light is also radiated on the production lot information identification 500 and sensed by the detector 703, in which the change in the intensity and wavelength of the light is converted into digital information. Then, the blue light is also radiated on the production lot information identification 500 and sensed by the detector 703, in which the change in the intensity and wavelength of the light is converted into digital information. The digital information, obtained by converting the light, is combined to provide production lot information as hue marks.

Conventionally, because many photodiodes emit light beams of various wavelengths simultaneously, which are then sensed by a detector, a process of scattering and filtering various wavelengths of the detected light using a spectrometer and a filter is required to identify the light information, which makes the calculation process thereof as well as the device and program thereof complicated. In contrast, the electrochemical biosensor measuring device according to the present invention is operated to emit light beams from photodiodes in a sequential manner, so that no filtering processes are required, obviating complicated computation processes. Thus, the electrochemical biosensor measuring device according to the present invention can be constructed to have a simple structure, which is economically favorable. In addition, with the insertion of the electrochemical biosensor thereinto, the electrochemical biosensor measuring device according to the present invention automatically identifies the production lot information of the biosensor, thus enabling blood glucose to be conveniently and accurately measured without a mistake being made by a user, and being economical.

The light emitter and the detector may be constructed in a separated or integrated structure. The detector may be located in the same plane as the light emitter when it is adapted to detect the light reflected from the hue marks, and may be located in a plane opposite the light emitter when it is adapted to detect the transmitted light.

The production lot information identification portion adapted for the electrochemical biosensor, which is used for the electrochemical biosensor measuring device according to the present invention, is not limited to a parallel type electrochemical biosensor, and may also be applied to a plane type electrochemical biosensor, which is implemented such that the working electrode and the auxiliary electrode are formed in the same plate and are thus operated, and to a differential type electrochemical biosensor, which is implemented such that the parallel type electrochemical biosensor and the plane type electrochemical biosensor process signals differently.

The electrochemical biosensor measuring device according to the present invention may be used along with a connector having a structure in which one or more absorption or reflection path(s), comprising light-emitting unit/production lot information identification portion/detector, can be realized, thereby identifying the production lot information marked on the biosensor.

The connector, for example, may be formed of a body having transparent material, such as transparent acrylic or plastic.

Furthermore, the connector may be provided with a transmission window in one side thereof so that infrared rays absorbed or reflected via the light-emitting unit/production lot information identification portion/detector are passed therethrough. Accordingly, even when the connector is made of opaque material or even when the body of the connector is colored, the light beams radiated by the light-emitting units can easily reach the production lot information identification portion of the biosensor through the transmission window, and thus the production lot information can be identified.

Furthermore, in order to pass the light beams, which are absorbed or reflected via light-emitting unit/production lot information identification portion/detector, through the connector, the connector may be manufactured such that one side thereof has a sliding door structure. In greater detail, when a biosensor is inserted into the connector, the sliding door structure of the connector is pushed along with the biosensor in the insertion direction of the biosensor, thus realizing the path along which the light beams can reach the production lot information identification portion of the biosensor. In this case, the sliding door structure may be connected to a device that can passively or automatically remove the biosensor, and thus the biosensor can be easily separated and removed from the biosensor measuring device using the removing device after the use of the biosensor.

The light emitting unit and detector used for the biosensor measuring device according to the present invention may be located inside or outside the connector of the measuring device. In greater detail, the light emitting unit and the detector may be integrated into the connector body, or may be used as structures that are separate from the connector body.

Furthermore, the present invention provides a measuring method using the electrochemical biosensor measuring device, comprising:

inserting a biosensor provided with a production lot identification portion containing production lot information into the connector port of the biosensor measuring device to activate its power (step 1);

identifying the production lot information of the inserted biosensor by allowing light emitting diodes to emit light beams having different wavelengths in a sequential manner and detecting the light beams with the production lot information identification portion provided in the biosensor (step 2);

activating the measurement and operation processes of the biosensor measuring device in conformity with the production lot information identified at Step 2 (step 3); and introducing a liquid sample to the sample inlet of the biosensor to result in quantitative electrochemical information about the sample, quantifying a specific component of the liquid sample, and displaying quantification results (step 4).

The measuring method using the biosensor measuring device of the present invention is described stepwise in detail below.

In step 1, a biosensor provided with a production lot identification portion containing production lot information into the connector port of the biosensor measuring device is inserted to activate its power.

As shown in FIG. 2, the biosensor is inserted into the measuring device through a sensor injection hole. Upon insertion, the electrodes 104 of the biosensor 110 are electrically connected to the electrical connection portions 705 of the connector to allow an electric current to flow, therefore operating the measuring device.

Next, Step 2 serves to identify the production lot information of the biosensor which is inserted at step 1. In this regard, light emitting diodes are allowed to emit light beams having different wavelengths in a sequential manner while the production lot information identification portion provided in the biosensor detects the light beams.

As shown in FIG. 2, the insertion of the biosensor 110 into the connector electrically connects the biosensor to the measuring device through the connector to activate the light emitter-detector system in the measuring device, thereby identifying the production lot information of the biosensor from the activated light emitter-detector system.

The production lot information identification portion may include one or more hue marks displaying the information about differences between production lots attributable to differences in color, brightness, or chroma. It is preferred that the number of hue marks be adjusted to fall within the range of 1 to 10.

The identification of the production lot information can be achieved as follows.

For instance, light beams are emitted sequentially from three-component photodiodes of red, green and blue colors or four-component photodiodes of white, red, green and blue colors to detect the hue marks of the production lot information identification portion. Variations in wavelength, color, brightness and chroma depending on the degrees of reflection or transmission of detected light beams are identified by an optical identification device and converted into digital information, so that the production lot information of the biosensor can be identified.

In Step 3, measurement and operation processes of the biosensor measuring device are activated in conformity with the production lot information identified at Step 2.

Following the identification of the production lot information in Step 2, in greater detail, the measuring device has measurement and operation processes activated in conformity with the identified production lot information, and enters a standby state for sample measurement.

Finally, Step 4 serves to introduce a liquid sample to the sample inlet of the biosensor to result in quantitative electrochemical information about the sample, quantify a specific component of the liquid sample, and display the quantified results.

In greater detail, the injection of a liquid sample into the biosensor strip inserted into the measuring device (step a) creates a predetermined potential difference between the working electrode and the auxiliary electrode and between the sample fluidity determining electrode and the auxiliary electrode (step b), the sample flowing into the sample introducing portion of the strip causes a primary electrical variation between the working electrode and the auxiliary electrode to adjust the voltages between the electrodes to the same value (step c). The sample fluidity determining electrode senses the flow of the sample to cause secondary electrical variation, and the voltage between the auxiliary electrode and the sample fluidity determining electrode is adjusted to be the same, thus providing information about the time difference with the electrical variation primarily sensed by the working electrode (step d). When a liquid sample is sufficiently mixed with a reagent applied to the working electrode, voltage is applied again between the working electrode and the auxiliary electrode to cause a cycling reaction in a parallel-type thin layer electrochemical cell, and the stationary current value thus reached is read (step e). The amount of the substrate present in the sample is analyzed using the time information obtained in step d and the stationary current value obtained in step e to determine the level of a specific component, such as blood glucose, and the result is displayed in a window.

As described hitherto, the electrochemical biosensor measuring device according to the present invention is characterized in that at least two photodiodes are made to emit light beams at regular time intervals in a sequential manner in order to identify the production lot information recorded on the production lot information identification portion on the electrochemical biosensor. Accordingly, the measuring device of the present invention has economic advantages over conventional devices in that it does not require a high-priced filter or a complicated calculation system. Furthermore, the measuring device automatically identifies the production lot information recorded on the biosensor, so that the inconvenience and error that occur when a user personally inputs the production lot information of the biosensor can be reduced, with the result that the measured values can be conveniently and accurately acquired.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A measuring method using an electrochemical biosensor measuring device and an electrochemical biosensor,
    wherein the biosensor is composed of a plurality of electrodes including at least a working electrode and an auxiliary electrode prepared on at least one or two insulating plates; a capillary sample cell for introducing a sample into the electrodes; a reaction reagent layer, formed on the working electrode, containing a redox enzyme and an electron transfer mediator; an electrical connection portion for connecting the working electrode and the auxiliary electrode; and a production lot information identification portion configured such that production lot information is recorded on at least one insulating plate, which is selected from among at least two planar insulating plates and does not interrupt a connection between the electrodes, wherein the production lot information identification portion includes one or more hue marks displaying the information about differences between production lots attributable to differences in color, brightness, or chroma,
    wherein the electrochemical biosensor measuring device comprises a connector having a connector port, at least two light emitters of which each emits a different color and a detector for sensing the emitted light,
    and the method comprising:
    inserting the biosensor into the connector port of the biosensor measuring device to activate its power (step 1);
    identifying the production lot information of the inserted biosensor by allowing said at least two light emitters to emit light beams having different wavelengths in a sequential manner at the production lot information identification portion and detecting the light beams with the production lot information identification portion provided in the biosensor (step 2),
    wherein the light beams emitted from the light emitters are sequentially detected by the detector without using a separate filter;
    activating the measurement and operation processes of the biosensor measuring device in conformity with the production lot information identified at Step 2 (step 3); and
    introducing a liquid sample to the sample inlet of the biosensor to result in quantitative electrochemical information about the sample, quantifying a specific component of the liquid sample, and displaying quantification results (step 4).

2. The measuring method according to claim 1, wherein the plurality of electrodes further include a sample fluidity determining electrode.

3. The measuring method according to claim 1, wherein the number of hue marks range from 1 to 10.

4. The measuring method according to claim 1, wherein said at least two light emitters are composed of three-component photodiodes that emit red, green and blue colors or four-components photodiodes that emit white, red, green and blue colors.

5. The measuring method according to claim 1, wherein the detector is an optical identification device.

6. The measuring method according to claim 1, wherein the light emitters and the detector are constructed in a separate or integrated structure.

7. The measuring method according to claim 1, wherein said at least two light emitters and the detector are integrated together with the body of the connector to identify the production lot information recorded in the biosensor, said body of the connector having a structure in which one or more absorption or reflection path(s) sequentially comprising a light-emitting unit, a production lot information identification portion and a detector, is (are) provided.

* * * * *